United States Patent [19]

Cook et al.

[11] Patent Number: 5,128,336
[45] Date of Patent: Jul. 7, 1992

[54] 3-(SUBSTITUTED)-1-CARBA(DETHIA)-3-CEPHEMS

[75] Inventors: Gwendolyn K. Cook; John H. McDonald, III, both of Indianapolis, Ind.

[73] Assignee: Eli Lilly and Company, Indianapolis, Ind.

[21] Appl. No.: 346,057

[22] Filed: May 1, 1989

Related U.S. Application Data

[62] Division of Ser. No. 172,091, Mar. 23, 1988, Pat. No. 4,855,418.

[51] Int. Cl.$^5$ .................. C07D 471/04; A61K 31/435
[52] U.S. Cl. ..................................... 514/210; 540/205
[58] Field of Search ...................... 540/205, 204, 310; 514/210

[56] References Cited

U.S. PATENT DOCUMENTS

| | | | |
|---|---|---|---|
| 4,226,866 | 10/1980 | Christensen et al. | 540/205 |
| 4,343,943 | 8/1982 | Hirata et al. | 540/205 |
| 4,520,022 | 5/1985 | Hoshi et al. | 514/200 |
| 4,537,886 | 8/1985 | Taylor et al. | 540/205 |
| 4,591,641 | 5/1986 | Hoshi et al. | 544/16 |
| 4,661,590 | 4/1987 | Hoshi et al. | 540/215 |
| 4,694,079 | 9/1987 | Crast, Jr. | 540/215 |
| 4,699,979 | 10/1987 | Hoshi et al. | 540/215 |
| 4,727,070 | 2/1988 | Kaplan et al. | 514/202 |
| 4,820,832 | 4/1989 | Cook et al. | 540/205 |
| 4,855,418 | 8/1989 | Cook et al. | 540/205 |

FOREIGN PATENT DOCUMENTS 0112481 7/1984 European Pat. Off. .

OTHER PUBLICATIONS

W. J. Scott, et al., "Palladium-Catalyzed Coupling of Vinyl Triflates With Organostannanes, a Short Synthetis of Pleraplysillin-I", *J. Am. Chem. Soc.*, 1984, 106, 4630-4632.

J. K. Stille, "The Palladium-Catalyzed Cross-Coupling Reactions of Organotin Reagents With Organic Electrophiles", *Angew. Chem. Int. Ed. Engl.*, 25 (1986) 508-524.

M. R. Pena and J. K. Stille, "Attachment of the Anthramycin Acrylamide Side Chain by the Palladium Catalyzed Coupling Reaction of a Vinyl Triflate", *Tetrahedron Letters*, vol. 28, No. 52, pp. 6573-6576, 1987.

F. Orsini and F. Pelizzoni, "Pd(O)-Mediated Cross--Coupling of Reformatsky Reagents With Vinyl- and Aryl Triflates", *Synthetic Comm.*, 17(12), 1389-1402 (1987).

A. M. Echavarren and J. K. Stille, "Palladium-Catalyzed Coupling of Aryl Triflates with Organostannanes", *J. Am. Chem. Soc.*, 1987, 109, 5478-5486.

H. M. Colquhoun, "Homogenous, Palladium-Catalyzed, Carbon-Carbon Bond Formation", *Chemistry and Industry*, Sep. 7, 1987, pp. 612-617.

E. Negishi et al., "Palladium- or Nickel-Catalyzed Rections of Alkenylmetals with Unsaturated Organic Halides as a Selective Route to Arylated Alkenes and Conjugated Dienes: Scope, Limitations and Mechanism", *J. Am. Chem. Soc.*, 1987, 2393-241.

J. K. Stille and J. H. Simpson, "Stereospecific Palladium-Catalyzed Coupling Reactions of Vinyl Iodides with Acetylenic tin Reagents", *J. Am. Chem. Soc.*, 1987, 109, 2138-2152.

T. N. Mitchell, "Transition-Metal Catalysts in Organotin Chemistry", *J. of Organometallic Chemistry*, 304 (1986) 1-16.

L. Castedo et al., "Palladium-Catalyzed Synthesis of Dienynes Related to Vitamin D From Enol Triflates", *Tetrahedron Letters*, vol. 27, No. 13, pp. 1523-1526.

J. K. Stille, "Palladium Catalyzed Coupling of Organotin Reagents With Organic Electrophiles", *Pure & Appl. Chem.*, vol. 57, No. 12, pp. 1771-1780, 1985.

W. J. Scott et al., "Palladium-Catalyzed Olefination of Vinyl Triflates", *J. Org. Chem.*, 1985, 50, 2302-2308.

W. J. Scott and J. K. Stille, "Palladium-Catalyzed Coupling of Vinyl Triflates With Organostannanes, Synthetic and Methanistic Studies", *J. Am. Chem. Soc.*, 1986, 108, 3033-3040.

L. A. Paquette et al., "Total Synthesis of (±)-Sterpuric Acid", *Tetrahedron Letters*, vol. 28, No. 92, pp. 5017-5020, 1987.

*Journal of the American Chemical Society*, 96, 7854 (1974).

*Journal of Medicinal Chemistry*, 20, 551 (1977).

*Primary Examiner*—Nicholas S. Rizzo
*Attorney, Agent, or Firm*—James J. Sales; Leroy Whitaker

[57] ABSTRACT

Cephalosporin and 1-carba(1-dethia)cephalosporin antibiotics substituted in the 3-position with, inter alia, alkyl, alkenyl and alkynyl, are provided via process comprising conversion of a cephalosporin or 1-carba(1-dethia)-3-cephem substituted in the 3-position with halogen or a sulfonyloxy ester with Pd(O) mediated alkylation with organostannanes.

10 Claims, No Drawings

3-(SUBSTITUTED)-1-CARBA(DETHIA)-3-CEPHEMS

This application is a division of application Ser. No. 07/172,901, filed Mar. 23, 1988 now U.S. Pat. No. 4,855,418.

BACKGROUND OF THE INVENTION

This invention relates to β-lactam antibiotics. In particular, it relates to certain 3-(substituted)-1-carba(dethia)-3-cephems and cephalosporin esters and to a process for the preparation thereof.

Among the newer β-lactam antibiotics currently under investigation are the 1-carba(1-dethia)-3-cephem-4-carboxylic acids. These β-lactam antibiotics provide significant synthetic challenges. Accordingly, one of the more noteworthy approaches to total synthesis of 1-carba(1-dethia)-3-cephem-4-carboxylic acids is the asymmetric route described by Evans, et al., U.S. Pat. No. 4,665,171. Thus, because these newer β-lactam antibiotics provide such synthetic challenges, the development of new processes are of considerable importance.

SUMMARY

7β-Acylamino(and 7β-protected amino)-3-alkyl(and alkenyl, phenyl, substituted phenyl, alkoxymethyl, phenylalkoxymethyl and alkynyl)-1-carba(1-dethia)-3-cephem-4-carboxylic acid esters are produced in a process comprising the Pd(0) mediated alkyl (alkenyl, phenyl, substituted phenyl, alkoxymethyl, phenylalkoxymethyl, trialkylsilyloxymethyl or alkynyl) transfer from an appropriately substituted organostannane to a 7β-acylamino(or 7β-protected amino)1-carba(1-dethia)-3-trifluoromethylsulfonyloxy(or mesyloxy, tosyloxy, chloro, bromo or iodo)-3-cephem ester or to the corresponding cephalosporin ester. The process provides certain 1-carba(1-dethia)-3-cephem esters (and cephem esters) which, in turn, may be deesterified to provide 1-carba(1-dethia)-3-cephem-4-carboxylic acid (or cephalosporin) antibacterials.

DETAILED DESCRIPTION OF THE INVENTION

The present invention provides a process for preparing a compound of Formula (1):

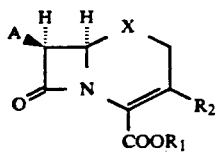

wherein A is a protected amino group or an acylamino group R(CO)—NH—; $R_1$ is a carboxy-protecting group or a biologically-labile ester; X is sulfur or —$CH_2$—; and $R_2$ is $C_1$–$C_6$ alkyl; $C_2$–$C_6$ alkenyl; $C_2$–$C_6$ alkynyl; $C_1$–$C_6$ substituted alkyl; $C_2$–$C_6$ substituted alkenyl; $C_2$–$C_6$ substituted alkynyl; phenyl; substituted phenyl; $C_1$–$C_6$ alkyloxymethyl; phenyl-$C_1$–$C_6$ alkyloxymethyl; or tri-($C_1$–$C_6$)alkylsilyloxymethyl; which comprises reacting a compound of Formula (2)

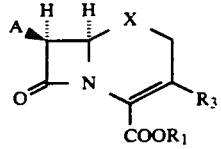

wherein A, X and $R_1$ are as defined above, and $R_3$ is trifluoromethylsulfonyloxy, methanesulfonyloxy, toluenesulfonyloxy, chloro, bromo or iodo; in an inert solvent in the presence of palladium(O) and, when $R_3$ is trifluoromethanesulfonyloxy, methanesulfonyloxy or p-toluenesulfonyloxy, in the presence of an alkali metal halide, with a tin transfer reagent of the formula tri($C_1$–$C_6$)alkyl-Sn-$R_2$ or Sn($R_2$)$_4$, wherein $R_2$ has the same meanings as defined above.

The term "alkali metal halide" herein refers to salts such as lithium chloride, lithium bromide, sodium chloride, sodium bromide and like salts. Lithium chloride is the preferred alkali metal halide. As one skilled in the art will appreciate, other halide sources, e.g., tetraalkylammonium halides such as tetramethyl ammonium chloride may be equally efficacious.

Inert solvents which may be employed include hexane, dimethylformamide, dimethylacetamide and like solvents which are capable of maintaining substantially all of the reagents and reactants in solution.

Examples of tin transfer reagents include tetramethylstannane, tetraethylstannane, tri-n-butyl vinyl stannane, tri-n-butyl allyl stannane, tri-n-butyl(methoxymethyl)stannane, tri-n-butyl ethynyl stannane, tri-n-butyl-[(Z)-1-propene-1-yl]stannane, tri-n-butyl[(Z)-3,3,3-trifluoro-1-propene-1-yl]stannane, tri-n-butyl(benzyloxymethyl)stannane, tri-n-butyl(2-propyne-1-yl)stannane and the like.

The above process is carried out at a temperature from about −70° C. to about 150° C., preferably from about 25° C. to about 75° C. under substantially anhydrous conditions and preferably in an inert atmosphere such as a nitrogen or argon atmosphere.

The "tin transfer reagent" of the formula tri($C_1$–$C_6$ alkyl)Sn-$R_2$ or Sn($R_2$)$_4$ is chosen by virtue of the desired $R_2$ substituent (3-position) in the β-lactam compound. As to the $C_1$–$C_6$ alkyl groups which may appear on the tin transfer reagent, n-butyl is preferred, i.e., tri-n-butyl tin-$R_2$ is the preferred reagent. Further, in some cases, it will be preferable to use a tin reagent of the formula Sn($R_2$)$_4$; for example, if the desired $R_2$ substituent is a simple alkyl such as methyl, Sn($CH_3$)$_4$ would be the preferred tin transfer reagent.

The palladium catalyst employed in the process is soluble or partially soluble Pd(O) which may be generated in situ or provided directly in the form of a palladium compound such as tetrakis-(triphenylphosphine)palladium(O). A reagent useful for generating Pd(O) in situ is palladium dichloride diacetonitrilate. . Other well-known palladium compounds which either exist as Pd(O) or can be reduced to Pd(O) in situ may be utilized if otherwise compatible with the reactants.

The process is performed by adding the palladium O compound or Pd(O) generating reagents, an alkali metal halide, when $R_3$ is other than halo, and a tin transfer reagent to a solution of the substrate (2) in an inert solvent. The reaction mixture is typically heated, if necessary, to complete the process. The progress of the reaction may be followed by thin layer chromatography or high-performance liquid chromatography using small aliquots of the reaction mixture from time to time. The resulting 3-substituted 1-carbadethia-3-cephem ester or cephalosporin ester (1) may then be recovered from the reaction mixture by conventional isolation techniques. For example, the reaction mixture may be diluted with a water immiscible solvent such as ethyl acetate, the solution washed sequentially with dilute acid and bicarbonate and, after drying, may be evaporated to provide the product (1) in crude form. Purification may then be effected using conventional methodology, for example, utilizing recrystallization and/or chromatography, e.g., high-performance liquid chromatography.

As described above when the process is carried out with a 3-sulfonyloxy derivative, e.g., trifluoromethyl sulfonyloxy, the addition of an alkali metal halide to the reaction mixture is necessary. Conversely, the 3-halo substituted starting materials are converted in the process without added alkali halide or other halide source.

In a general example of the process, palladium dichloride diacetonitrilate (approximately 0.1 molar equivalent) and lithium chloride (2.0 molar equivalents) are dissolved in dimethylformamide. The reaction mixture is then cooled in an ice bath and benzhydryl-7μ-phenoxyacetylamino-1-carba(1-dethia)-3-trifluormethylsulfonyloxy- 3-cephem-4-carboxylate is added followed by the stannane $(CH_3CH_2CH_2CH_2)_3Sn-C\equiv C-CH_3$. After the reaction is complete, conventional isolation and purification techniques provide benzhydryl-7β-phenoxyacetyl-1-carba(1-dethia)-3-(1-propynyl)-3-cephem-4-carboxylate in good yield.

Preferred starting materials (2) include compounds wherein $R_3$ is bromo, iodo or trifluoromethanesulfonyloxy.

Some examples of the 3-substituted cephalosporins and 1-carba(1-dethia)-3-cephems produced by the process include p-nitrobenzyl-7β-phenoxyacetylamino-3-(cis-1-propenyl)-3-cephem-4-carboxylate; p-nitrobenzyl-7β-phenoxyacetylamino-1-carba(1-dethia)-3-(cis-1-propenyl)-3-cephem-4-carboxylate; benzhydryl-7β-phenoxyacetylamino-3-vinyl-3-cephem-4-carboxylate; benzhydryl-7β-phenylacetylamino-1-carba(1-dethia)-3-vinyl-3-cephem-4-carboxylate; p-nitrobenzyl-7β-phenoxyacetylamino-3-(benzyloxy)methyl-3-cephem-4-carboxylate; and p-nitrobenzyl-7β-phenoxyacetylamino-1-carba(1-dethia)-3-(benzyloxy)methyl-3-cephem-4-carboxylate; benzhydryl 7β-t-butyloxycarbonylamino-1-carba(1-dethia)-3-vinyl-3-cephem-4-carboxylate; p-nitrobenzyl 7β-t-butyloxycarbonylamino-1-carba(1-dethia)-3-vinyl-3 3-cephem-4-carboxylate; benzhydryl 7β-t-butyloxycarbonylamino-1-carba(1-dethia)-3-(cis)-(1-propene-1-yl)-3-cephem-4-carboxylate; and p-nitrobenzyl-7β-t-butyloxycarbonylamino-1-carba(1-dethia)-3-(cis)-(1-propene-1-yl)-3-cephem-4-carboxylate.

The 1-carba-3-trifluoromethylsulfonyloxy esters of Formula (2) which are used as the starting materials in the process may be prepared by the method of Evans, et al., U.S. Pat. No. 4,673,737. The other starting materials of Formula (2) wherein $R_3$ is tosylate, mesylate or halo are likewise known compounds synthesized by known methodology.

In Formula (1), when A is an acylamino group R(CO)NH—, R is hydrogen; $C_1$-$C_6$ alkyl, $C_1$-$C_6$ alkyl substituted by cyano, carboxy, halogen, amino, $C_1$-$C_4$ alkoxy, $C_1$-$C_4$ alkylthio, or trifluoromethylthio; a phenyl or substituted phenyl group represented by the formula

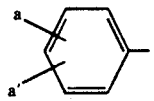

wherein a and a' independently are hydrogen, halogen, hydroxy, $C_1$-$C_4$ alkoxy, $C_1$-$C_4$ alkanoyloxy, $C_1$-$C_4$ alkyl, $C_1$-$C_4$ alkylthio, amino, mono- or di($C_1$-$C_4$ alkyl)amino, $C_1$-$C_4$ alkanoylamino, $C_1$-$C_4$ alkylsulfonylamino, carboxy, carbamoyl, hydroxymethyl, aminomethyl, or carboxymethyl;

a group represented by the formula

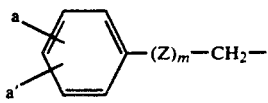

wherein a and a' have the same meanings as defined above, Z is O or S, and m is 0 or 1;

a heteroarylmethyl group represented by the formula $R^1-CH_2-$ wherein $R^1$ is thienyl, furyl, benzothienyl, benzofuryl, indolyl, triazolyl, tetrazolyl, oxazolyl, thiazolyl, oxadiazolyl, thiadiazolyl, and such heteroaryl groups substituted by amino, hydroxy, halogen, $C_1$-$C_4$ alkyl, $C_1$-$C_4$ alkoxy, $C_1$-$C_4$ alkylsulfonylamino;

a substituted methyl group represented by the formula

wherein $R_2$ is cyclohex-1,4-dienyl, or a phenyl group or substituted phenyl group represented by the formula

wherein a and a' have the above defined meanings, or $R^2$ is $R^1$ as defined above, and Q is hydroxy, $C_1$-$C_4$ alkanoyloxy, carboxy, sulfo, or amino;

or R is a keto group or an oximino-substituted group represented by the formulae

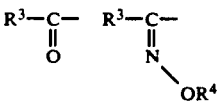

wherein $R^3$ is $R^1$ or $R^2$ as defined above and $R^4$ is hydrogen, $C_1$-$C_4$ alkyl, or a carboxy-substituted alkyl or cycloalkyl group represented by the formula

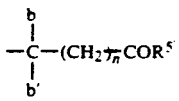

wherein b and b' independently are hydrogen, or $C_1$–$C_3$ alkyl, and b and b' when taken together with the carbon to which they are bonded form a 3- to 6-membered carbocyclic ring, and $R^5$ is hydroxy, $C_1$–$C_4$ alkoxy, amino, $C_1$–$C_4$ alkylamino, or di($C_1$–$C_4$ alkyl)amino.

In the above definitions, $C_1$–$C_6$ alkyl refers to the straight and branched chain alkyl groups such as methyl, ethyl, n-propyl, isopropyl, n-butyl, t-butyl, n-pentyl, n-hexyl, 3-methylpentyl, and like alkyl groups; $C_1$–$C_6$ alkyl substituted by cyano refers to cyanomethyl, cyanoethyl, 4-cyanobutyl, and the like; $C_1$–$C_6$ alkyl substituted by carboxy refers to such groups as carboxymethyl, 2-carboxyethyl, 2-carboxypropyl, 4-carboxybutyl, 5-carboxypentyl, and the like; $C_1$–$C_6$ alkyl substituted by halogen refers to chloromethyl, bromomethyl, 2-chloroethyl, 1-bromoethyl, 4-chlorobutyl, 4-bromopentyl, 6-chlorohexyl, 4-fluorobutyl, 3-fluoropropyl, fluoromethyl, and the like; $C_1$–$C_6$ alkyl substituted by amino refers to such groups as 2-aminoethyl, aminomethyl, 3-aminopropyl and 4-aminobutyl; $C_1$–$C_6$ alkyl substituted by $C_1$–$C_4$ alkoxy refers to methoxymethyl, 2-methoxyethyl, 2-ethoxyethyl, ethoxymethyl, 3-propoxypropyl, 3-ethoxybutyl, 4-t-butyloxybutyl, 3-methoxypentyl, 6-methoxyhexyl, and like group; $C_1$–$C_6$ alkyl substituted by $C_1$–$C_4$-alkylthio refers to such groups as for example methylthiomethyl, 2-methylthioethyl, 2-ethylthiopropyl, 4-methylthiobutyl, 5-ethylthiohexyl, 3-t-butylthiopropyl, and like groups; $C_1$–$C_6$ alkyl substituted by trifluoromethyl is exemplified by 2,2,2-trifluoroethyl, 3,3,3-trifluoropropyl, 4,4,4-trifluorobutyl, and the like; and $C_1$–$C_6$ alkyl substituted by trifluoromethylthio refers to, for example, trifluoromethylthiomethyl, 2-trifluoromethylthioethyl, 2-trifluoromethylthiopropyl, 4-trifluoromethylthiobutyl, 5-trifluoromethylthiohexyl, and like $C_1$–$C_6$ alkyl substituted groups.

When in Formula (1) R is a substituted phenyl group wherein the substituent(s) are represented by a and a', examples of such groups are halophenyl such as 4-chlorophenyl, 3-bromophenyl, 2-fluorophenyl, 2,4-dichlorophenyl, and 3,5-dichlorophenyl; hydroxyphenyl such as 2-hydroxyphenyl, 3-hydroxyphenyl, 4-hydroxyphenyl, 2,4-dihydroxyphenyl, and 3,4-dihydroxyphenyl; alkoxyphenyl, such as 2,6-dimethoxyphenyl, 4-methoxyphenyl, 3-ethoxyphenyl, 3,4-dimethoxyphenyl, 4-t-butyloxyphenyl, 4-methoxy-3-ethoxyphenyl, and 4-n-propoxyphenyl; alkanoyloxyphenyl such as 2-acetoxyphenyl, 4-propionoxyphenyl, 4-formyloxyphenyl, 4-acetoxyphenyl, 3-butyryloxyphenyl, and 3-acetoxyphenyl; alkylphenyl such as 4-methylphenyl, 2-methylphenyl, 2,4-dimethylphenyl, 3-t-butylphenyl, 4-ethylphenyl, 4-ethyl-3-methylphenyl, and 3,5-dimethylphenyl; alkylthiophenyl such as 4-methylthiophenyl, 3-n-butylthiophenyl, 2-ethylthiophenyl, 3,4-dimethylthiophenyl, and 3-n-propylthiophenyl; aminophenyl such as 2-aminophenyl, 4-aminophenyl, 3,5-diaminophenyl, and 3-aminophenyl; alkanoylamino such as 2-acetylamino, 4-acetylamino, 3-propionylamino, and 4-butyrylamino; alkylsulfonylamino such a 3-methylsulfonylamino, 4-methylsulfonylamino, 3,5-(dimethylsulfonylamino)phenyl, 4-n-butylsulfonylaminophenyl, and 3-ethylsulfonylaminophenyl; carboxyphenyl such as 2-, 3-, or 4-, carboxyphenyl, 3,4-dicarboxyphenyl, and 2,4-dicarboxyphenyl; carbamoylphenyl such as 2-carbamoylphenyl, 2,4-dicarbamoylphenyl, and 4-carbamoylphenyl; hydroxymethylphenyl such as 4-hydroxymethylphenyl and 2-hydroxymethylphenyl; aminomethylphenyl such as 2-aminomethylphenyl and 3-aminomethylphenyl; and carboxyphenyl such as 2-carboxymethylphenyl, 4-carboxymethylphenyl, and 3,4-dicarboxymethylphenyl; and the substituted phenyl groups bearing different substituents such as 4-chloro-3-methylphenyl, 4-fluoro-3-hydroxyphenyl, 3,5-dichloro-4-hydroxyphenyl, 4-hydroxy-3-chlorophenyl, 4-hydroxy-3-methylphenyl, 4-ethyl-3-hydroxyphenyl, 4-methoxy-3-hydroxyphenyl, 4-t-butyloxy-2-hydroxyphenyl, 4-acetylamino-3-methoxyphenyl, 3-amino-4-ethylphenyl, 2-aminomethyl-4-chlorophenyl, 2-hydroxymethyl-3-methoxyphenyl, 2-hydroxymethyl-4-fluorophenyl, 2-acetoxy-4-aminophenyl, 4-acetoxy-3-methoxyphenyl, 3-isopropylthio-4-chlorophenyl, 2-methylthio-4-hydroxymethylphenyl, 4-carboxy-3-hydroxyphenyl, 4-ethoxy-3-hydroxyphenyl, 4-methylsulfonylamino-2-carboxyphenyl, 4-amino-3-chlorophenyl, and 2-carboxymethyl-4-hydroxyphenyl.

Examples of RCONH— groups of Formula (1) wherein R is a group represented by the formula

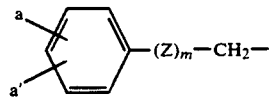

with $m=0$ are: phenylacetyl, 4-hydroxyphenylacetyl, 4-chlorophenylacetyl, 3,4-dichlorophenylacetyl, 4-methoxyphenylacetyl, 3-ethoxyphenylacetyl, 2-aminomethylphenylacetyl, 3-carboxyphenylacetyl, 4-acetoxyphenylacetyl, 3-aminophenylacetyl, and 4-acetylaminophenylacetyl; and with $m=1$ and $Z=0$, phenoxyacetyl, 4-chlorophenoxyacetyl, 4-fluorophenoxyacetyl, 3-aminophenoxyacetyl, 3-hydroxyphenoxyacetyl, 2-methoxyphenoxyacetyl, 2-methylthiophenoxyacetyl, 4-acetylaminophenoxyacetyl, 3,4-dimethylphenoxyacetyl, and 3-hydroxymethylphenoxyacetyl; and with $m=1$ and $Z=S$, phenylthioacetyl, 4-chlorophenylthioacetyl, 3,4-dichlorophenylthioacetyl, 2-fluorophenylthioacetyl, 3-hydroxyphenylthioacetyl, and 4-ethoxyphenylthioacetyl.

Examples of $R^1$—$CH_2CONH$-groups of Formula (1) wherein $R^1$ is a heteroaryl group are: 2-thienylacetyl, 3-thienylacetyl, 2-furylacetyl, 2-benzothienylacetyl, 2-benzofurylacetyl, indol-2-ylacetyl, 1H-tetrazol-1-ylacetyl, oxazol-2-ylacetyl, oxazol-4-ylacetyl, thiazol-4-ylacetyl, 2-aminothiazol-4-ylacetyl, 1,3,4-oxadiazol-2-ylacetyl, 1,3,4-thiadiazol-2-ylacetyl, 5-ethyl-1,3,4-thiadiazol-2-ylacetyl, and like heteroaryl groups optionally substituted by amino, $C_1$–$C_4$ alkylsulfonylamino, hydroxy, halo, $C_1$–$C_4$ alkyl or $C_1$–$C_4$-alkoxy groups.

Examples of RCONH— groups of Formula (1) compounds wherein R is a substituted methyl group represented by the formula $R^2$—CH(Q)— and Q is amino, carboxy, hydroxy, or sulfo, are 2-carboxy-2-phenylacetyl, 2-carboxy-2-(4-hydroxyphenyl)acetyl, 2-amino-2-phenylacetyl, 2-amino-2-(4-hydroxyphenyl)acetyl, 2-amino-2-(3-chloro-4-hydroxyphenyl)acetyl, 2-amino-2-(cyclohex-1,4-dien-1-yl)acetyl, 2-hydroxy-2-phenylacetyl, 2-formyloxy-2-phenylacetyl, 2-sulfo-2-phenylacetyl, 2-sulfo-2-(4-methylphenyl)acetyl, and 2-acetoxy-2-(3-hydroxyphenyl)acetyl, 2-amino-2-(2-thienyl)acetyl, 2-amino-2-(3-benzothienyl)acetyl, 2-amino-2-(1H-tetrazol-1-yl)acetyl, 2-hydroxy-2-(1,3,4-thiadiazol-2-yl)acetyl, 2-amino-2-(2-aminothiazol-4-yl)acetyl, 2-carboxy-2-(2-thienyl)acetyl, 2-carboxy-2-(benzothien-2-yl)acetyl, and 2-hydroxy-2-(benzofur-2-yl)acetyl.

Examples of RCONH— acyl groups of the compounds represented by Formula (1) when R is a keto group or an oximino-substituted group represented by the formulae

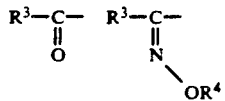

are the keto groups 2-oxo-2-phenylacetyl, 2-oxo-2-(2-thienyl)acetyl, 2-oxo-2-(2-aminothiazol-4-yl)acetyl; and oximino-substituted groups 2-phenyl-2-methoxyiminoacetyl, 2-(2-thienyl)-2-ethoxyiminoacetyl, 2-(2-furyl-2-methoxyiminoacetyl, 2-(2-benzothienyl)-2-carboxymethoxyiminoacetyl, 2-(2-thienyl)-2-(2-carboxyethoxy)iminoacetyl, 2-(2-amino-1,2,4-thiadiazol-4-yl)-2-methoxyiminoacetyl, 2-(2-aminothiazol-4-yl)-2-methoxyiminoacetyl, 2-(2-chlorothiazol-4-yl)-2-methoxyiminoacetyl, 2-(2-aminothiazol-4-yl)-2-(2-carboxyprop-2-yl)oxyiminoacetyl, 2-(2-aminothiazol-4-yl)-2-(2-carbamoylprop-2-yl)oxyiminoacetyl, and 2-(5-amino-1,3,4-thiadiazol-2-yl)-2-methoxyiminoacetyl.

The starting material (2) desirably has any free amino or carboxy functions which may be present in the R(CO) group in protected form, e.g., protected with an $R_1$ protecting group or a protected amino group as defined below.

The carboxy-protecting group $R^1$ is a conventional carboxy-blocking group used in the β-lactam antibiotic art and serves the function of blocking the acidic carboxy group while reactions are carried out at other sites in the molecule. Such groups are used for the temporary protection or blocking of the carboxy group. Examples of such groups are t-butyl, haloalkyl groups, e.g. 2,2,2-trichloroethyl, 2-iodoethyl, benzyl, substituted benzyl, e.g. 4-nitrobenzyl, and 4-methoxybenzyl, diphenylmethyl, trialkylsilyl or mixed alkylarylsilyl groups, e.g. trimethylsilyl, triethylsilyl, dimethylphenylsilyl, β-trimethylsilylethyl, and β-methylsulfonylethyl. Preferred carboxy-protecting groups are 4-nitrobenzyl and diphenylmethyl.

The term "biologically-labile ester" refers to those biologically active ester forms which induce increased blood levels and prolong the efficacy of the corresponding non-esterified forms of the compounds. Such ester groups include the lower alkoxymethyl groups, for example, methoxymethyl, ethoxymethyl, iso-propoxymethyl and the like; the α-($C_1$ to $C_4$)alkoxyethyl groups, for example, methoxyethyl, ethoxyethyl, propoxyethyl, iso-propoxyethyl and the like; the 2-oxo-1,3-dioxolen-4-ylmethyl groups, such as 5-methyl-2-oxo-1,3-dioxolen-4-ylmethyl, 5-phenyl-2-oxo-1,3-dioxolen-b 4-ylmethyl and the like; and $C_1$ to $C_1$ alkylthiomethyl groups, for example, methylthiomethyl, ethylthiomethyl, iso-propylthiomethyl and the like; the acyloxymethyl groups, for example, pivaloyloxymethyl, α-acetoxymethyl and the like; the ethoxycarbonyl-1-methyl group; the α-acyloxy-α-substituted methyl groups, for example, α-acetoxyethyl; the 3-phthalidyl or 5,6-dimethylphthalidyl groups; the 1-($C_1$ to $C_4$ alkyloxycarbonyloxy)eth-1-yl groups such as the 1-(ethoxycarbonyloxy)eth-1-yl group; and the 1-($C_1$ to $C_4$ alkylaminocarbonyloxy)eth-1-yl groups such as the 1-(methylaminocarbonyloxy)eth-1-yl group.

Protected amino groups represented by A in Formulae (1) and (2) are the conventional protecting or blocking groups attached to an amino group, which are used in the β-lactam antibiotic art for the temporary protection of the amino group function while reactions at other sites in the molecule are carried out. Examples of suitable protecting groups are formyl, trichloroacetyl, tribromoacetyl, trityl, an alkyl, cycloalkyl, or aryloxycarbonyl group such as ethoxycarbonyl, t-butyloxycarbonyl, trichloroethoxycarbonyl, cyclopentyloxycarbonyl, benzyloxycarbonyl, p-nitrobenzyloxycarbonyl, and diphenylmethoxycarbonyl; allyloxycarbonyl, a bicyclooxycarbonyl group such as adamantyloxycarbonyl or bicycloheptyloxycarbonyl; an enamine group such as that formed from a free amine and methylacetoacetate or ethylacetoacetate; or other conventional amino-protecting group. Preferred protected amino groups A are represented by the formula

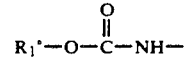

wherein $R°_1$ is $C_1$-$C_4$-alkyl, $C_3$-$C_7$ cycloalkyl, benzyl, nitrobenzyl, halobenzyl or methoxybenzyl. Preferred protected amino groups are benzyloxycarbonylamino, p-nitrobenzyloxycarbonylamino, and t-butyloxycarbonylamino.

The 3-substituted esters (1) obtained in the process of this invention may be deesterified to provide the free $C_4$ carboxylic acid antibiotics. Accordingly, the 7-substituent may be changed or derivatized to provide other β-lactam antibiotics.

In a preferred aspect of the process, A is t-butoxycarbonylamino, phenoxyacetylamino or phenylacetylamino, and X is carbon. In a further preferred aspect of the process, A is t-butoxycarbonylamino, phenoxyacetylamino, phenylacetylamino; X is sulfur; and $R_2$ is (cis)prop-1-ene-1-yl.

As used herein, the term $C_2$ to $C_6$ alkenyl refers to straight and branched olefins. Examples of the term $C_2$ to $C_6$ alkenyl include ethenyl, 1-propenyl, 2-propene-1-yl, 1-butene-1-yl, 2-butene-1-yl, 3-butene-1-yl, 1-pentene-1-yl, 2-pentene-1-yl, 3-pentene-1-yl, 4-pentene-1-yl, 1-hexene-1-yl, 2-hexene-1-yl, 3-hexene-1-yl, 4-hexene-1-yl, 5-hexene-1-yl, isopropene-1-yl, isobutenyl, isopentenyl, isohexenyl and the like.

A preferred subgroup of the term $C_2$ to $C_6$ alkenyl is a group of the formula $C_3$ to $C_6$ alkenyl.

As used herein, the term $C_2$ to $C_6$ substituted alkenyl refers to a $C_2$ to $C_6$ alkenyl group substituted by one or more halogen, hydroxy, protected hydroxy, nitro or trihalomethyl groups. It will, of course, be appreciated that a free hydroxy group may need to be protected during the course of the process as taught herein. Preferred $C_2$ to $C_6$ substituted alkenyl groups are (Z)-3,3,3-trifluoro-1-propene-1-yl and (Z)-1-propene-1-yl.

As used herein, the term $C_2$ to $C_6$ alkynyl refers to straight and branched acetylenic groups. Examples of the term $C_2$ to $C_6$ alkynyl include ethynyl, 1-propyne-1-yl, 2-propyne-1-yl, 1-butyne-1-yl, 2-butyne-1-yl, 3-butyne-1-yl, 1-pentyne-1-yl, 2-pentyne-1-yl, 3-pentyne-1-yl, 4-pentyne-1-yl, 1-hexyne-1-yl, 1-hexyne-1-yl, 3-hexyne-1-yl, 4-hexyne-1-yl, 5-hexyne-1-yl, 2-methyl-2- propyne-1-yl, 2-methyl-4-propyne-1-yl, 2-methyl-3-pentyne-1-yl, 2-methyl-3-butyne-1-yl and the like.

As used herein, the term $C_2$ to $C_6$ substituted alkynyl refers to a $C_2$ to $C_6$ alkynyl group substituted by one or more halogen, hydroxy, protected hydroxy, nitro or trihalomethyl.

As used herein, the term substituted phenyl denotes the same groups as defined hereinabove for the term R.

Examples of the term $C_1$ to $C_6$ alkyloxymethyl include methyloxymethyl, ethyloxymethyl, n-propyloxymethyl, n-butyloxymethyl, n-pentyloxymethyl, n-hexyloxymethyl, isopropyloxymethyl, isobutyloxymethyl, isopentyloxymethyl, isohexyloxymethyl and the like.

Examples of the term phenyl $C_1$ to $C_6$ alkyloxymethyl include benzyloxymethyl, (2-phenyl)ethyloxymethyl, (3-phenyl)-n-propyloxymethyl, (4-phenyl)-n-butyloxymethyl, (5-phenyl)-n-pentyloxymethyl, (6-phenyl)-n-hexyloxymethyl, (2-phenyl)(2-methyl)ethyloxymethyl, (3-phenyl)(3-methyl)-n-propyloxymethyl and the like.

In a further aspect of the present invention, there are provided compounds of Formula (3):

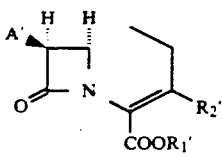

(3)

wherein A' is amino or A as defined above for Formula (1); $R_2'$ is $C_2$ to $C_6$ alkenyl, $C_2$ to $C_6$ alkynyl, $C_2$ to $C_6$ substituted alkenyl, $C_2$ to $C_6$ substituted alkynyl or a group of the formula —$CH_2$—O—$SiR'R''R'''$, wherein R', R" and R'" are the same or different and are $C_1$ to $C_6$ alkyl; and $R_1'$ is hydrogen, a carboxy-protecting group, a biologically-labile ester; or, when $R_1'$ is hydrogen, a pharmaceutically-acceptable salt thereof.

Preferred compounds are represented by Formula (3), wherein $R_2'$ is $C_2$-$C_6$ alkenyl group. Particular preferred groups are represented when $R_2'$ is vinyl or a propenyl group of the formula

wherein $R_4$ is methyl or trihalomethyl. An especially preferred embodiment of the present invention are the compounds of Formula (3) wherein $R_2'$ is a group of the formula

and $R_4$ is trifluoromethyl.

Compounds of Formula (3) wherein $R_1'$ is hydrogen can be prepared by deesterification of the corresponding compound of Formula (2), wherein $R_1$ is a carboxy-protecting group, by utilization of conventional methodology.

Among the preferred compounds are those wherein A is R(C))—NH— and R is

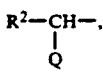

especially where Q is amino and $R^2$ is phenyl, hydroxyphenyl or cyclohexdienyl. An especially preferred compound is 7β-phenylglycylamino-3-(Z)(2-propenyl)-1-carba(1-dethia)-3-cephem-4-carboxylic acid.

The 1-carbacephalosporins provided by the invention form salts with suitable bases, in particular, the pharmaceutically-acceptable, non-toxic salts. The C-4 carboxy group of the 1-carbacephalosporin can form salts with the alkali and alkaline earth metal hydroxides, carbonates and bicarbonates. Examples of such pharmaceutically-acceptable salts are the sodium, potassium, calcium and magnesium salts. Salts also may be formed with amines such as dibenzylamine, cyclohexylamine, triethylamine, ethanolamine, di-ethanolamine and like amines. Likewise, when the 1-carbacephalosporin is substituted by two or more carboxy groups, di- and tri-salts are obtained by conventional salt-forming methods.

1-Carbacephalosporin compounds represented by Formula (3) which bear an amino group substituent in the 7-position side chain also form salts with suitable acids to provide the antibiotics as pharmaceutically-acceptable salts. Examples of suitable acids are hydrochloric, hydrobromic, sulfuric and phosphoric.

The pharmaceutically-acceptable, non-toxic salts are useful forms of the antibiotics for preparing antibiotic formulations.

This invention also provides a method for treating infectious diseases in man and animals and pharmaceutical formulations suitable for administration in the treatment method. The therapeutic method of this invention comprises administering to a man or other animals an antibiotically effective non-toxic dose of a compound represented by Formula (1) wherein $R_2$ is hydrogen or a pharmaceutically acceptable salt or biologically labile ester thereof.

An antibiotically effective amount is an amount between about 25 mg and about 2 grams. The compound, salt or ester may be administered in a single dose or in multiple doses throughout the day. Treatment may continue for a week to ten days or longer depending upon the duration of the infection. The particular dose and regimen can depend on such factors as the weight and age of the patient, the particular causative organism, the severity of the infection, the general health of the patient, and the tolerance of the individual to the antibiotic.

The 1-carbacephalosporins may be administered parenterally, orally, subcutaneously or rectally. As with other β-lactam antibiotics, the method of this invention may be used prophylactically to prevent infections after exposure or before possible exposure, e.g., preoperatively. The antibiotic 1-carbacephalosporins may be administered by conventional methods, e.g., in capsules, tablets, by syringe, or by intravenous drip.

The pharmaceutical formulations of the invention comprise an antibiotically effective non-toxic amount of a 1-carbacephalosporin represented by Formula (1) wherein $R_2$ is hydrogen, a pharmaceutically acceptable non-toxic salt or biologically labile ester thereof, and a pharmaceutical carrier.

Formulations for oral administration include capsules, tablets, lozenges and liquid suspensions. The antibiotic or a salt or ester thereof in the form of a dry powder is encapsulated in gelatin capsules for oral use. The antibiotic may also be blended with an excipient, e.g., a stabilizer, prior to filling. Capsules may contain between about 100 mg and about 500 mg to provide unit dosage formulations.

Tablets containing between about 100 mg and 500 mg of the antibiotic or a salt or ester thereof are formulated by conventional means and may contain in addition a binding agent, disintegrating agent, stabilizing agent, antioxidant, etc.

Liquid preparations of the antibiotic may be prepared for infant and geriatric use. Pediatric suspensions are formulated with the antibiotic oral excipients such as suspending agents, flavoring agents, stabilizers and the like. Solutions of the antibiotics likewise may be formulated with solubilizing agents, flavoring agents, sugar, water, etc.

Parenteral formulations of the antibiotics for injection are formulated with Water-for-Injection, Ringer's solution, physiological saline or glucose solution. The antibiotic also may be administered in an intravenous fluid by the drip method.

For parenteral use the antibiotic, a salt or biologically labile ester thereof, is made up preferably in dry crystalline powder form or as a lyophilized powder and filled into vials. Such vials contain between about 100 mg and about 2 grams of antibiotic per vial.

The following experimental section provides further examples of the various aspects of the present invention but is not to be construed as limiting the scope therefor.

EXPERIMENTAL SECTION

Preparation 1

Palladium dichloride diacetonitrilate

A 20 g sample of palladium dichloride was dissolved in 375 ml of $CH_3CN$, stirred under $N_2$ and heated to reflux for 0.5 h. The insoluble material was filtered off and the filtrate set aside. The title compound crystallized upon standing from the above filtrate. Filtration followed by drying at room temperature under reduced pressure provided 7.23 g of the title compound.

EXAMPLE 1 p-Nitrobenzyl-7$\beta$-phenoxyacetylamino-3-vinyl-3-cephem-4-carboxylate

To a solution of 1 ml of dimethylformamide was added 282 g (0.5 mmol) of p-nitrobenzyl 7-$\beta$-phenoxyacetylamino-3-methanesulfonyloxy-3-cephem-4-carboxylate, 87 mg (1.00 mmol) of lithium bromide and 6.5 mg (0.025 mmol) of palladium dichloride diacetonitrilate and the solution stirred under $N_2$. The reaction mixture was treated with 161 $\mu$l (0.55 mmol) of tri-n-butyl vinyl tin, stirred for 16 h, and then treated with an additional 6 mg of palladium dichloride diacetonitrilate. After an additional 3 h of stirring, the reaction mixture was diluted with water and extracted with ethyl acetate. The ethyl acetate portion was then washed (2$\times$) with water and concentrated in vacuo. The crude residue was then dissolved in acetonitrile and washed (3$\times$) with hexane. Removal of solvent in vacuo, followed by liquid chromatography (gradient elution: 3% ethyl acetate/$CH_2Cl_2$ to 5% ethyl acetate/$CH_2Cl_2$) provided 130 mg of the title compound.

NMR (300 MHz, TMS, $CDCl_3$): 3.55 (d,1H); 4.60 (s, 2H); 5.05 (d, 1H); 5.40 (d, 1H); 5.53 (d, 1H); 5.92 (d of d, 1H); 6.94 (br d, 2H); 7.0-7.4 (m, 7H); 7.59 (d, 2H); 8.22 (d, 2H).

Preparation 2

(Z)-tri-n-Butyl-(1-propenyl)stannane (Reference: J. F. Normant, *Org. Syn.*, Vol. 62, page 1).

A 4.32 g (0.021 mole) sample of $CuBr.(CH_3)_2S$ was dissolved in 40 ml of anhydrous diethyl ether and cooled to $-50°$ C. under argon. Next, a 78.4 ml sample of a 0.51 molar solution of methyl lithium (in diethyl ether) was added dropwise (via syringe) at such a rate so as to maintain the temperature of the reaction mixture at or below $-20°$ C. After addition was complete, the reaction was stirred at $-30°$ C. for 20 minutes and then treated (under the reaction mixture surface) with a constant stream of acetylene for 15 minutes, while maintaining the temperature of the reaction mixture at or below $-25°$ C. Stirring is then continued for an additional 25 minutes, followed by saturation of the reaction mixture with argon to remove unreacted acetylene.

The resulting cuprate solution was then cooled to $-60°$ C. and maintained between $-50°$ C. and $-60°$ C. while 13.0 ml (15.62 mg; 0.048 moles, 1.2 molar equivalents) of tri-n-butyl tin chloride (dissolved in 30 ml of anydrous diethyl ether) was added The reaction mixture was then allowed to warm to room temperature overnight.

The resulting reaction mixture was cooled, quenched with saturated $NH_4Cl$ solution and filtered through Celite. The inorganic layer was washed with hexane and the combined organic phases were washed sequentially with saturated $NH_4Cl$ solution and brine, dried over anhydrous $NH_4SO_4$, filtered and concentrated in vacuo. The resulting crude material was distilled through a Vigreaux column (91°–94° C./0.25 mm Hg) to provide 3 5 g of the title compound as a clear oil.

EXAMPLE 2 p-Nitrobenzyl-7$\beta$-phenoxyacetylamino-3-(cis-1-propenyl)-3-cephem-4-carboxylate A 274 mg (0.5 mmol) sample of p-nitrobenzyl-7$\beta$-phenoxyacetylamino-3-bromo-3-cephem-4-carboxylate and 8.5 mg (0.032 mmol) sample of palladium dichloride diacetontrilate were dissolved in 1 ml of anhydrous dimethylformamide Under $N_2$, the reaction mixture was treated with tri-n-butyl, cis(1-propenyl)stannane and stirred at room temperature for 1 h. At this point, no reaction had occurred, so another 8.5 mg of palladium dichloride diacetonitrilate was added and the reaction mixture heated slightly. The reaction mixture was then allowed to stir overnight.

The resulting crude product mixture was poured into water and extracted with (1:1) ethyl acetate/diethyl ether. The resulting organic phase was then washed with water and concentrated in vacuo. The crude product was dissolved in $CH_3CN$ and extracted with hexane (3$\times$). Removal of solvent in vacuo, followed by flash chromatography over silica (5% ethyl acetate/$CH_2Cl_2$ as eluent) provided 162 mg (64% yield) of the title compound.

NMR (300 MHz, TMS, $CDCl_3$) $\delta$: 1.60 (br d, 3H); 3.38 (d, 1H); 3.55 (d, 1H); 4.57 (s, 2H); 5.10 (d, 1H); 5.25-5.40 (m, 3H); 5.66-5.77 (m, 1H); 5.90 (d of d, 1H); 6.17 (br d, 1H); 6.92 (d, 2H); 7.03 (t, 1H); 7.2-7.4 (m, 3H); 7.60 (d, 2H); 8.21 (d, 2H).

EXAMPLE 3 p-Nitrobenzyl-7$\beta$-phenoxyacetylamino-3-ethenyl-3-cephem-4-carboxylate

In a manner analogous to that of Example 3 (i.e., tri-n-butylethenyl stannane was used as the tin transfer reagent), the title compound was produced from the 3-bromo-3-cephem ester.

NMR (300 MHz, TMS, CDCl₃) δ: 3.55 (d, 1H); 4.60 (s, 2H); 5.05 (d, 1H); 5.40 (d, 1H); 5.53 (d, 1H); 5.92 (d of d, 1H); 6.94 (br d, 2H); 7.0–7.4 (m, 7H); 7.59 (d, 2H); 8.22 (d, 2H).

EXAMPLE 4

Benzhydryl-7β-phenoxyacetylamino-1-carba(1-dethia)-3-methyl-3-cephem-4-carboxylate A 2 mg (0.008 mmol) sample of palladium dichloride diacetonitrilate and 13 mg (0.318 mmol) of lithium chloride were dissolved in 0.26 ml of dimethylformamide. To this solution was added a 10 mg (0.159 mmol) sample of benzhydryl 7β-phenoxyacetylamino-1-carba(1-diethia)-3-trifluoromethanesulfonyloxy-3-cephem-4-carboxylate followed by 31 mg (24 μl; 0.175 mmol) of tetramethyl stannane. The reaction mixture was then stirred under N₂ for 10 minutes. At that time, the reaction mixture was treated with an additional 2 mg of palladium dichloride diacetonitrilate (repeated after 10 additional minutes). Finally, an additional 2.0 molar equivalents of tetramethyl stannane and 2 mg of palladium dichloride diacetonitrilate were added and the reaction mixture was heated to 35° C. Shortly thereafter the reaction was complete. The crude product mixture was diluted with CH₃CN was washed (3×) with hexane. The CH₃CN solution was then evaporated in vacuo and the crude product redissolved in ethyl acetate/diethyl ether (1:1). The resulting solution was then washed (3×) with water, filtered and evaporated in vacuo. The crude product was chromatographed over silica gel (5% ethyl acetate/CH₂Cl₂ as eluent) to provide 55 mg (70% yield) of the title compound.

NMR (300 MHz, CDCl₃): 1.30–1.44 (1H, m); 1.70–1.80 (1H, m); 1.94 (3H, s); 2.14–2.27 (2H, m); 3.74–3.80 (1H, m); 4.50 (2H, s); 5.30–5.37 (1H, m); 6.80–6.94 (2H, m); 6.94 (1H, t); 7.14–7.47 (14H, m).

EXAMPLE 5

Benzhydryl-7β-phenoxyacetylamino-1-carba(1-dethia)-3-vinyl-3-cephem-4-carboxylate A 2.00 g (3.17 mmol) sample of benzhydryl 7β-phenoxyacetylamino-1-carba(1-dethia)-3-methanesulfonyloxy-3-cephem-4-carboxylate, 41 mg (0.16 mmol) of palladium dichloride diacetonitrilate, and 295 mg (6.34 mmol) of lithium chloride were dissolved in 6.3 ml of anhydrous dimethylformamide and the solution was stirred under N₂. The reaction mixture was then treated with 1.02 ml (3.49 mmol) of tri-n-butyl vinyl tin over a one-minute period. After about 10 minutes the reaction was diluted with H₂O and an (1:1) ethyl acetate/diethyl ether mixture. The organic phase was removed and washed (2×) with water. The solvent was then removed in vacuo and the crude product residue . redissolved into CH₃CN. The CH₃CN solution was washed (3×) with hexane and concentrated in vacuo. Chromatography over silica gel (100% CH₂Cl₂ to 2% ethyl acetate/CH₂Cl₂ to 5% ethyl acetate/CH₂Cl₂ gradient elution) provided 1.46 g (91% yield) of the title compound.

NMR (300 MHz, CDCl₃): 1.19–1.37 (1H, m); 1.72–1.87 (1H, m); 2.07–2.22 (1H, m); 2.57 (1H, doublet of doublets); 3.74–3.85 (1H, m); 4.47 (2H, s); 5.17 (1H, d); 5.30–5.43 (2H, m); 6.77–6.87 (3H, m); 6.93 (7H, t); 7.07–7.43 (14H, m).

EXAMPLE 6

Benzhydryl-7β-phenoxyacetylamino-1-carba(1-dethia)-3-(2-methyl-1-propene-1-yl)-3-cephem-4-carboxylate In a procedure analogous to that utilized in Example 5, substituting tri-n-butyl (2-methyl-1-propene-1-yl)tin as the tin transfer reagent, the title compound was produced with the same 1-carba(dethia)ester as starting material in 76% yield.

NMR (CDCl₃) δ: 1.29–1.45 (4H, m); 1.59 (3H, s); 1.79–1.92 (1H, m); 2.09–2.25 (1H, m); 2.26–2.39 (1H, m); 3.82–3.89 (1H, m); 4.49 (2H, s); 5.35 (1H, doublet of doublets); 5.75 (1H, s); 6.82–6.89 (2H, m); 6.95 (1H, t); 7.04 (1H, d); 7.15–7.39 (13H, m).

EXAMPLE 7

Benzhydryl-7β-phenoxyacetylamino-1-carba(1-dethia)-3-(cis-prop-1-ene-1-yl)-3-cephem-4-carboxylate In a procedure analogous to that utilized in Example 5, substituting tri-n-butyl(cis(1-propene-1-yl))tin as the tin transfer reagent and utilizing the same starting material, the title compound was produced in 88% yield.

NMR (CDCl₃) δ: 1.40–1.48 (4H, m); 1.90–2.0 (1H, m); 2.26–2.40 (1H, m); 2.40–2.52 (1H, m); 2.88–3.98 (1H, m); 4.54 (2H, s); 5.44 (1H, doublet of doublets); 5.46–5.60 (1H, m); 6.13 (1H, d); 6.90–6.96 (2H, m); 7.06 (1H, t); 7.11 (1H, d); 7.22–7.48 (13H, m).

|      | λ   | ε      |
| ---- | --- | ------ |
| U.V. | 285 | 9270.0 |
|      | 276 | 9760.0 |
|      | 269 | 9120.0 |

| Elemental Analysis: | | |
| --- | --- | --- |
|  | Theory | Found |
| C (%) | 73.55 | 73.30 |
| H (%) | 5.79 | 5.75 |
| N (%) | 5.36 | 5.22 |

EXAMPLE 8

Benzhydryl-7β-phenoxyacetylamino-1-carba(1-dethia)-3-(prop-1-yne-1-yl)-3-cephem-4-carboxylate In a procedure analogous to that utilized in Example 5, substituting tri-n-butyl(1-propyene-1-yl)tin as the tin transfer reagent and utilizing the same starting material, the title compound was produced in 61% yield.

NMR (300 MHz, CDCl₃) δ: 1.32–1.42 (1H, m); 1.82–1.93 (1H, m); 1.96 (3H, s); 2.38–2.60 (2H, m); 3.80–3.88 (1H, m); 4.54 (2H, s); 5.42 (1H, doublet of doublets); 6.88–6.96 (2H, m); 6.98–7.06 (2H, m); 7.18 (1H, d); 7.20–7.54 (12H, m).

U.V.: λ=2.97 nm (ε=16,400).

I.R.: β-lactam C=O: 1772.2 cm⁻¹.

EXAMPLE 9

Benzhydryl-7β-phenoxyacetylamino-1-carba(1-dethia)-3-methoxymethyl-3-cephem-4-carboxylate In a procedure analogous to that utilized in Example 5, substituting tri-n-butyl(methoxymethyl)tin as the tin transfer reagent utilizing the same starting material, the title compound was produced in 58% yield.

NMR (300 MHz, CDCl₃) δ: 1.13–1.30 (1H, m); 1.59–1.77 (1H, m); 2.07–2.23 (1H, m); 2.24–2.33 (1H, m); 3.10 (3H, s); 3.67–3.77 (1H, m); 4.07–4.27 (2H, m); 4.43 (2H, s); 5.10–5.37 (1H, m); 6.77–6.93 (4H, m); 7.10–7.47 (18H, m).

EXAMPLE 10

Benzhydryl-7β-phenoxyacetylamino-1-carba(1-dethia)-3-benzyloxymethyl-3-cephem-4-carboxylate In a procedure analogous to that utilized in Example 5, substituting tri-n-butyl(benzyloxymethyl)tin as the tin transfer reagent and utilizing the same starting material, and at a temperature of about 65°–70° C., the title compound was produced in 41% yield.

NMR (300 MHz, CDCl$_3$) δ: 1.15–1.32 (1H, m); 1.70–1.80 (1H, m); 2.13–2.30 (1H, m); 2.33–2.47 (1H, m); 3.70–3.80 (1H, m); 4.17–4.53 (6H, m); 5.30–5.37 (1H, m); 6.77–7.07 (2H, m); 6.93 (1H, t); 7.13–7.50 (19H, m).

EXAMPLE 11 p-Nitrobenzyl-7β-phenoxyacetylamino-1-carba(1-dethia)-3-(t-butyldimethylsilyloxy)methyl-3-cephem-4-carboxylate In a procedure analogous to that utilized in Example 5, substituting tri-n-butyl[(t-butyl dimethylsilyl)oxy]methyl stannane as the tin transfer reagent and utilizing the same starting material, and at a temperature of about 65°–70° C., the title compound was produced in 25% yield.

NMR (300 MHz, CDCl$_3$) δ: 0.50 (6H, s); 0.87 (9H, s); 1.30–1.45 (1H, m); 1.90–2.08 (1H, m); 2.30–2.48 (1H, m); 2.50–2.67 (1H, m); 3.83–3.95 (1H, m); 4.40–4.71 (4H, m); 5.20–5.45 (3H, m); 6.90 (2H, d); 7.00–7.10 (2H, m); 7.23–7.37 (2H, m); 7.60 (2H, d); 8.23 (2H, d).

EXAMPLE 12

Benzhydryl 7β-1-carba(1-dethia)-3-(2-methyl-1-propene-1-yl)-3-cephem-4-carboxylate A 200 mg sample of benzyhydryl-7β-D[-t-butoxycarbonylamino)phenylglycylamido]-1-carba(1-dethia)-3-trifluoromethylsulfonyloxy- 3-cephem-4-carboxylate and 29 mg (0.685 mmol) of lithium chloride and 7.1 mg (0.0274 mmol) of palladium dichloride diacetonitrilate was dissolved in 2.74 ml of dry dimethylformamide under N$_2$. The reaction mixture was then treated with tri-n-butyl (2-methyl-1-propene-1-yl)tin. After about 15 minutes the reaction mixture was dilsuted with water and a (1:1) ethyl acetate/diethyl ether mixture. The organic phase was washed (3×) with water and once with brine, dried over anhydrous MgSO$_4$, filtered and concentrated in vacuo. The crude product was then redissolved in CH$_3$CN and washed (4×) with hexane. The CH$_3$CN solution was concentrated in vacuo and chromatographed (6% ethyl acetate/CH$_2$Cl$_2$ to 10% ethyl acetate/CH$_2$Cl$_2$ gradient elution) over silica gel to provide 275 mg (79% yield) of the title compound.

NMR (300 MHz, CDCl$_3$) δ: 0.93–1.10 (1H, m); 1.20–1.43 (13H, m); 1.53–1.66 (4H, m); 2.03–2.13 (1H, m); 3.68–3.78 (1H, m); 5.03–5.13 (1H, m); 5.28 (1H, doublet of doublets); 5.60 (1H, d); 5.70 (1H, s); 6.43 (1H, broad s); 6.80 (1H, s); 7.13–7.38 (16H, m).

EXAMPLE 13

Benzhydryl 7β-phenoxyacetylamino-1-carba(1-dethia)-3-(2,2-difluoroethene-1-yl)-3-cephem-4-carboxylate In a procedure analogous to that utilized in Example 5 (temperature ~35° C.), substituting tri-n-butyl (2,2-difluoroethene-1-yl)stannane as the tin transfer reagent and utilizing benzhydryl 7β-phenoxyacetylamino- 1-carba(1-dethia)-3-trifluoromethanesulfonyloxy-3-cephem-4-carboxylate as starting material, the title compound was produced.

NMR (300 MHz, CD$_3$CN) δ: 1.60–1.77 (1H, m); 1.83–1.97 (1H, m); 2.40–2.55 (1H, m); 2.63–2.78 (1H, m); 3.80–3.96 (1H, m); 4.53 (2H, s); 5.55 (1H, doublet of doublets); 6.0 (1H, doublet of doublets); 6.83 (1H, s); 6.90–7.10 (3H, m); 7.20–7.63 (13H, m).

We claim:

1. A compound of the formula

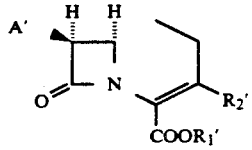

wherein A' is an acylamino group of the formula R(CO)—NH—, wherein R is hydrogen, $C_1$–$C_6$ alkyl, $C_1$–$C_6$ alkyl substituted by cyano, carboxy, halogen, amino, $C_1$–$C_4$ alkoxy, $C_1$–$C_4$ alkylthio, or trifluoromethylthio; a phenyl or substituted phenyl group represented by the formula

wherein a and a' independently are hydrogen, halogen, hydroxy, $C_1$–$C_4$ alkoxy, $C_1$–$C_4$ alkanoxyloxy, $C_1$–$C_4$ alkyl, $C_1$–$C_4$ alkylthio, amino, mono- or di($C_1$–$C_4$ alkyl)amino, $C_1$–$C_4$ alkanoylamino, $C_1$–$C_4$ alkylsulfonylamino, carboxy, carbamoyl, hydroxymethyl, aminomethyl or carboxymethyl;

a group represented by the formula

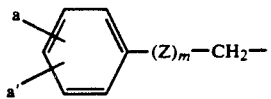

wherein a and a' have the same meanings as defined above, Z is O or S, and m is 0 or 1;

a heteroarylmethyl group represented by the formula

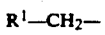

wherein $R^1$ is thienyl, furyl, benzothienyl, benzofuryl, indolyl, triazolyl, tetrazolyl, oxazolyl, thiazolyl, oxadiazolyl, thiadiazolyl, and such heteroaryl groups substituted by amino, hydroxy, halogen, $C_1$–$C_4$ alkyl, $C_1$–$C_4$ alkoxy or $C_1$–$C_4$ alkylsulfonylamino;

a substituted methyl group represented by the formula

wherein $R^2$ is cyclohex-1,4-dienyl, or a phenyl group or substituted phenyl group represented by the formula

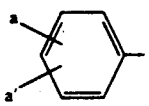

wherein a and a' have the above-defined meanings, or $R^2$ is $R^1$ as defined above, and Q is hydroxy, $C_1-C_4$ alkanoyloxy, carbonyl, sulfo, or amino;
or R is a keto group or an oximino-substituted group represented by the formulae

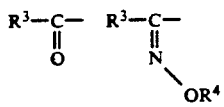

wherein $R^3$ is $R^1$ or $R^2$ as defined above and $R^4$ is hydrogen, $C_1-C_4$ alkyl, or a group represented by the formula

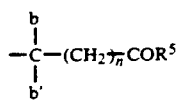

wherein b and b' independently are hydrogen, or $C_1-C_3$ alkyl, and b and b' when taken together with the carbon to which they are bonded form a 3- to 6-membered carbocyclic ring, and $R^5$ is hydroxy, $C_1-C_4$ alkoxy, amino, $C_1-C_4$ alkylamino or di($C_1-C_4$ alkyl)amino and n is 0 or 1;
$R^2$ is $C_2-C_6$ alkenyl, $C_2-C_6$ alkynyl, $C_2-C_6$ alkenyl substituted by one or more halogen, hydroxy, protected hydroxy, nitro, or trihalomethyl, $C_2-C_6$ alkynyl substituted by one or more halogen, hydroxy, protected hydroxy, nitro, or trihalomethyl, or a group of the formula $-CH_2-O-SiR'R''R'''$, wherein R', R'' and R''' are the same or different and are $C_1-C_6$ alkyl; and $R_1'$ is hydrogen or a biologically-labile ester; or a pharmaceutically-acceptable salt thereof.

2. A compound of the formula

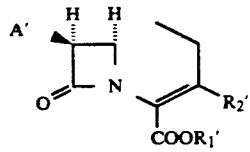

wherein A' is an acylamino group of the formula $R(CO)-NH-$, wherein R is hydrogen, $C_1-C_6$ alkyl, $C_1-C_6$ alkyl substituted by cyano, halogen, amino, $C_1-C_4$ alkoxy, $C_1-C_4$ alkylthio, or trifluoromethylthio; a phenyl or substituted phenyl group represented by the formula

wherein a and a' independently are hydrogen, halogen, hydroxy, $C_1-C_4$ alkoxy, $C_1-C_4$ alkanoyloxy, $C_1-C_4$ alkyl, $C_1-C_4$ alkylthio, amino, mono- or di($C_1-C_4$ alkyl)amino, $C_1-C_4$ alkanoylamino, $C_1-C_4$ alkylsulfonylamino, carboxy, carbamoyl, hydroxymethyl, aminomethyl or carboxymethyl;
a group represented by the formula

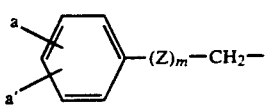

wherein a and a' have the same meanings as defined above, Z is O or S, and m is 0 or 1;
a heteroarylmethyl group represented by the formula

wherein $R^1$ is thienyl, furyl, benzothienyl, benzofuryl, indolyl, triazolyl, tetrazolyl, oxazolyl, thiazolyl, oxadiazolyl, thiadiazolyl, and such heteroaryl groups substituted by amino, hydroxy, halogen, $C_1-C_4$ alkyl, $C_1-C_4$ alkoxy or $C_1-C_4$ alkylsulfonylamino;
a substituted methyl group represented by the formula

wherein $R^2$ is cyclohex-1,4-dienyl, or a phenyl group or substituted phenyl group represented by the formula

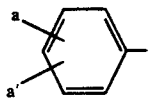

wherein a and a' have the above-defined meanings, or $R^2$ is $R^1$ as defined above, and Q is hydroxy, $C_1-C_4$ alkanoyloxy, carbonyl, sulfo, or amino;
or R is a keto group or an oximino-substituted group represented by the formulae

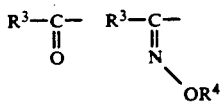

wherein $R^3$ is $R^1$ or $R^2$ as defined above and $R^4$ is hydrogen, $C_1-C_4$ alkyl, or a group represented by the formula

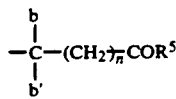

wherein b and b' independently are hydrogen, or $C_1-C_3$ alkyl, and b and b' when taken together with the carbon to which they are bonded form a 3- to 6-membered carbocyclic ring, and $R^5$ is hydroxy, $C_1-C_4$ alkoxy, amino, $C_1-C_4$ alkylamino or di($C_1-C_4$ alkyl)amino and n is 0 or 1;
$R^{2'}$ is $C_2-C_6$ alkyl, $C_2-C_6$ alkynyl, $C_2-C_6$ alkenyl substituted by one or more halogen, hydroxy, protected hydroxy, nitro, or trihalomethyl, or a group of the formula $-CH_2-O-SiR'R''R'''$, wherein R', R'' and R''' are the same or different and are $C_1-C_6$ alkyl; and $R_1'$ is hydrogen or a biologically-labile ester; or a pharmaceutically-acceptable salt thereof.

3. A compound of claim 2, wherein $R_2'$ is a group of the formula

and $R_4$ is methyl or trihalomethyl.

4. A compound of claim 3 wherein $R_4$ is trifluoromethyl.

5. A method for treating bacterial infection in man or other animals which comprises administering an antibacterially-effective amount of an antibiotic of claim 2 wherein $R_2'$ is hydrogen or a pharmaceutically-acceptable salt or biologically-labile ester thereof.

6. An antibacterial pharmaceutical formulation comprising an efficacious amount of a compound of claim 2 and a pharmaceutically-acceptable carrier.

7. A compound of claim 1, wherein $R_2'$ is a group of the formula

and $R_4$ is methyl or trihalomethyl.

8. A compound of claim 7, wherein $R_4$ is trifluoromethyl.

9. A method for treating bacterial infections in man or other animals which comprises administering an antibacterially-effective amount of an antibiotic of claim 1, wherein $R_2'$ is hydrogen and $A'$ is an acylamino group of the formula R(CO)—NH—, or a pharmaceutically-acceptable salt or biologically-labile ester thereof.

10. An antibacterial pharmaceutical formulation comprising an efficacious amount of a compound of claim 1, and a pharmaceutically-acceptable carrier.

* * * * *

UNITED STATES PATENT AND TRADEMARK OFFICE
CERTIFICATE OF CORRECTION

PATENT NO. : 5,128,336

DATED : July 7, 1992

INVENTOR(S) : Gwendolyn K. Cook and John H. McDonald, III

It is certified that error appears in the above-indentified patent and that said Letters Patent is hereby corrected as shown below:

On the title page, in the Abstract, line 2, "inter alia" should be underlined.

Column 1, line 21, "et al", should be underlined.

Column 2, lines 55-60 all occurrences of "in situ" should be underlined.

Column 5, line 11 after the word "alkylamino," add --and n is 0 or 1--.

Column 7, line 61, "and $C_1$ to $C_1$" should read --the $C_1$ to $C_3$--

Column 8, line 40 "In a further preferred" should start a new paragraph.

Column 9, lines 22-29 delete the structural formula therein and insert therefor:

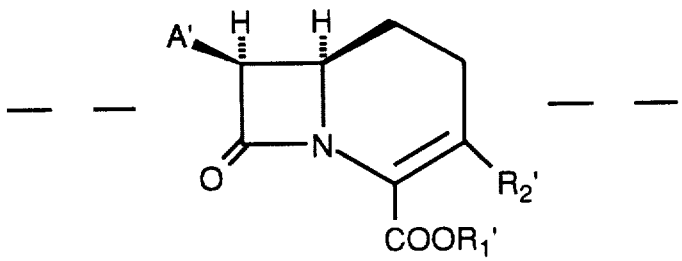

Column 11, line 23, "experimental section" should read --Experimental Section--.

Column 11, lines 53-55 all occurrences of "in vacuo" should be underlined.

Column 12, lines 49-51 all occurrences of "in vacuo" should be underlined.

Column 13, line 14 "(1-diethia)" should read --(1-dethia)--.

Column 13, lines 28-32 all occurrences of "in vacuo" should be underlined.

UNITED STATES PATENT AND TRADEMARK OFFICE
CERTIFICATE OF CORRECTION

PATENT NO. : 5,128,336

DATED : July 7, 1992

INVENTOR(S) : Gwendolyn K. Cook and John H. McDonald, III

It is certified that error appears in the above-indentified patent and that said Letters Patent is hereby corrected as shown below:

Column 13, lines 56-58 all occurrences of "in vacuo" should be underlined.

Column 15, lines 48-50 all occurrences of "in vacuo" should be underlined.

Column 16, lines 11-19 delete the structural formula therein and insert therefor:

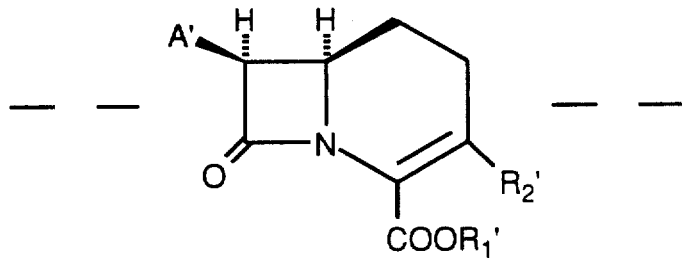

Column 17, lines 44-51 delete the structural formula therein and insert therefor:

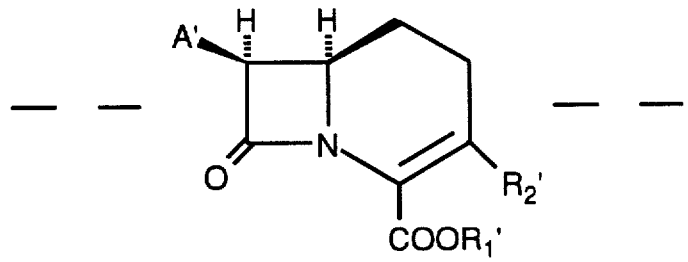

UNITED STATES PATENT AND TRADEMARK OFFICE
CERTIFICATE OF CORRECTION

PATENT NO. : 5,128,336

DATED : July 7, 1992

INVENTOR(S) : Gwendolyn K. Cook and John H. McDonald, III

It is certified that error appears in the above-indentified patent and that said Letters Patent is hereby corrected as shown below:

Column 18, line 64 delete "$C_2$-$C_6$ alkenyl".

Column 19, line 12 the word "infection" should read --infections--.

Signed and Sealed this

Thirty-first Day of May, 1994

BRUCE LEHMAN

Attest:

*Attesting Officer*      *Commissioner of Patents and Trademarks*